(12) United States Patent
Paronen et al.

(10) Patent No.: US 10,588,314 B2
(45) Date of Patent: Mar. 17, 2020

(54) SURFACES WHICH STAY MICROBIOLOGICALLY CLEAN

(71) Applicant: Stiftelsen Arcada, Helsinki (FI)

(72) Inventors: Mikael Paronen, Espoo (FI); Valeria Poliakova, Helsinki (FI); Simo-Pekka Toivonen, Helsinki (FI)

(73) Assignee: Stiftelsen Arcada, Helsinki (FI)

( * ) Notice: Subject to any disclaimer, the term of this patent is extended or adjusted under 35 U.S.C. 154(b) by 0 days.

(21) Appl. No.: 14/916,598

(22) PCT Filed: Sep. 4, 2014

(86) PCT No.: PCT/FI2014/050678
§ 371 (c)(1),
(2) Date: Mar. 4, 2016

(87) PCT Pub. No.: WO2015/033024
PCT Pub. Date: Mar. 12, 2015

(65) Prior Publication Data
US 2016/0198707 A1    Jul. 14, 2016

(30) Foreign Application Priority Data
Sep. 4, 2013 (FI) ...................................... 20135894

(51) Int. Cl.
| A01N 43/36 | (2006.01) |
| A01N 37/00 | (2006.01) |
| A01N 25/34 | (2006.01) |
| A61L 2/232 | (2006.01) |
| A01N 25/10 | (2006.01) |

(52) U.S. Cl.
CPC ............. *A01N 43/36* (2013.01); *A01N 25/10* (2013.01); *A01N 25/34* (2013.01); *A01N 37/00* (2013.01); *A61L 2/232* (2013.01)

(58) Field of Classification Search
CPC ....................................................... A61L 2/232
See application file for complete search history.

(56) References Cited

U.S. PATENT DOCUMENTS

| 5,882,667 A | 3/1999 | Jones |
| 6,939,569 B1 | 9/2005 | Green et al. |
| 2003/0059456 A1 | 3/2003 | Malcolm et al. |
| 2010/0263793 A1* | 10/2010 | Ylitalo ................... A01N 25/34 156/714 |
| 2011/0238163 A1* | 9/2011 | Andrews ............... A61L 29/085 623/1.46 |
| 2016/0206769 A1* | 7/2016 | Zeiger ................... A01N 59/20 |

FOREIGN PATENT DOCUMENTS

| EP | 0290739 A2 | 11/1988 |
| EP | 0453112 A1 | 10/1991 |
| EP | 2110018 A1 | 10/2009 |
| JP | H1121400 A | 1/1999 |
| WO | WO2006013374 A2 | 2/2006 |
| WO | WO2007067494 A1 | 6/2007 |
| WO | WO2011129982 A2 | 10/2011 |

OTHER PUBLICATIONS

Primo Spiro Product Data, "PrimoSpire PR-120", Solvay Advanced Polymers, 2006.*

Bressy, C. et al., "Poly(trialkylsilyl methacrylate)s: A family of hydrolysable polymers with tuneable erosion profiles", Polymer Degradation and Stability 95, pp. 1260-1268, 2010.

Mistry et al: Development of LDPE-based antimicrobial films for food packaging a thesis submitted in fulfilment of the requirements for the award of masters degree. Master Thesis, Jan. 6, 2006. pp. 1-112 XP055207688.

Varshosaz et al: Composite poly(vinyl alcohol)/poly(vinyl acetate) electrospun nanofibrous mats as a novel wound dressing matrix for controlled release of drugs. International Journal of Nanomedicine, May 19, 2011. vol. 6, pp. 993-1003. XP055524071.

* cited by examiner

*Primary Examiner* — Gina C Justice
(74) *Attorney, Agent, or Firm* — Seppo Laine Oy

(57) ABSTRACT

An antimicrobial composition which comprises an active agent that reduces the spread of pathogens. The active agent is mixed with a water-soluble polymer in order to form a mixture, in which the polymer forms a continuous phase, from which the active agent is capable of being released. The composition can be used to produce objects, for example elongated extrudates, which can be used to cover and coat different objects. Thus, the surface is constantly covered with the active agent until the object is mechanically worn away.

10 Claims, 1 Drawing Sheet

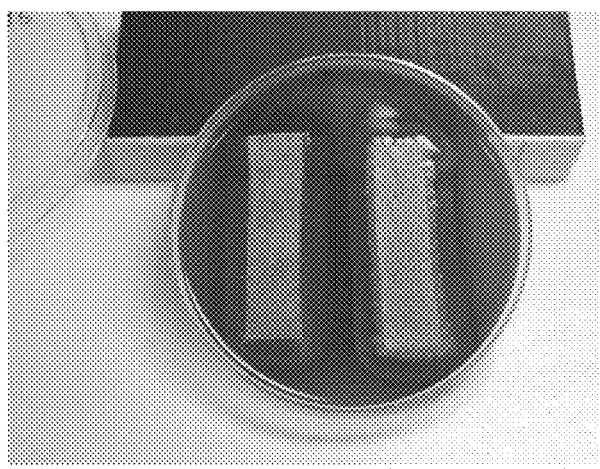

SURFACES WHICH STAY MICROBIOLOGICALLY CLEAN

The present invention relates to an antimicrobial composition, which comprises an active agent that reduces the spread of pathogens.

A composition such as this comprises in general an active agent that reduces exposure to pathogens.

The present invention further relates to a substrate that remains microbiologically clean and a method for preparing an antimicrobial composition.

Different objects are exposed to dirt in almost all functional environments. Impurities can accumulate on the surfaces of the objects, for example as a result of air flow, gravity or physical contact. These contamination mechanisms may be associated, regarding the actual attachment and adhesion to the surface, with a large number of chemical and physical mechanisms.

Accumulation of impurities on surfaces usually leads to impaired functionality and functional unreliability of the surfaces. As a result of these, hazardous surfaces must be cleaned and this results in significant additional costs for maintenance. However, it is not possible to maintain adequate cleanliness of all surfaces and, consequently, surface contamination results in both excessive costs and needless hazards.

The contamination accumulated on the surfaces of the objects can be divided into two different categories, i.e. macroscopic material and microbiologically significant material. Macroscopic contamination can be comprised of almost all possible organic and inorganic material, and combinations thereof. Microbiological material, however, is comprised of microbes and their spores. The most problematic group of microbiological material are agents causing diseases, that is pathogens. Their significant mechanism of infection is based on physical contact, either directly with the pathogen carrier, or indirectly: the recipient of the infection touches a surface which has been previously touched by the pathogen carrier. Thus, in the worst case, direct or indirect contact leads to a transfer of a pathogen to another person, who then falls ill.

The actual risk of falling ill by exposure through indirect contact is most evidently relatively small, because of the defense system of the human body.

However, indirect contacts occur to such an extent that the risk of infection they cause is very high—according to some estimates, approximately 70% of the infectious diseases which are transferred from one person to another are based on indirect contact. Surfaces that cause infections are those which are often touched by people, for example handrails, door handles, furniture, electrical switches and keyboards. In fact, microbiologically contaminated surfaces, i.e. fomites, have a clear effect on the spread of infectious diseases. Therefore, especially in hospitals and healthcare facilities, and also day nurseries and schools, proper hand hygiene is required in order to reduce microbial infections: microbes which accumulate on the hands end up, due to people's natural behavior, on the mucous membranes (in the mouth and nose) and, consequently, also cause infections and illnesses.

The most expensive and the most problematic area of disease among the population is related to pathogens. In quantitative terms, the main pathogen-related problems are catching a common cold and influenza, and also epidemics caused by the norovirus. In addition, there are a number of special cases which typically result in high mortality or exceptionally large costs of resolving or managing problems—probably the most well-known example of this group is related to hospital bacterial strains, such as the MRSA bacterial strains.

The usual way to avoid infections in health care facilities is to clean the surfaces with a micro-fiber cloth that has been moistened with an antimicrobial agent. The method is a temporary solution, and the effects of this disinfection disappear immediately after a microbiologically contaminated person touches the surface. The frequency of contacts can be very large and therefore, in practice, the benefit of manual disinfection of surfaces is at best minimal. Accordingly, avoiding infections via fomites requires continuous decontamination of the surfaces.

Deactivation of pathogens on surfaces can also be achieved by other methods. Thus, the objects can be heated either in dry air or by using water vapor, both of which, when implemented correctly, will lead to the destruction of the pathogens. In addition, surfaces and objects can be for example irradiated by way of ionizing radiation, which in turn achieves a corresponding deactivation of the pathogens.

Besides using physical methods, decontamination can also be carried out chemically: the object to be cleaned and its surface are brought into contact with a chemically reactive material, which leads to destruction of the pathogens. Suitable chemical substances can be pure forms of elements, or their oxidized forms or chemical compounds. Chemical decontamination can be based on a partial or total destruction of the structure of the pathogen, for example through a chemical reaction, precipitation or dissolution. Well-known chemical disinfection agents are for example ozone, polyethylene oxide, alcohols, peroxides, acids and bases, transition element metals and precious metals (for example Cu or Ag), halogens and their derivatives, as well as quaternary ammonium compounds.

Thus, treatments of objects and their surfaces result in surfaces that are sufficiently cleaned of pathogens, but a new contamination may occur as soon as the next person touches the surface. This period of time may last for only a few seconds. Thus, the effects of thorough cleaning are almost immediately lost.

A large number of solutions for continuously operating decontamination and disinfection have been developed. These include, for example:

Physical cleaning

Chemical cleaning agent, doped for example in a polymer (Teflon, PE, PDMS)

However, these solutions are either technically cumbersome (for example an UV lamp requires a power supply, and exposes people to UV radiation), or their functionality is completely dependent on whether the disinfecting agent is always able to reliably destroy the pathogens.

In known chemical solutions, such as the one described in U.S. Pat. No. 5,882,667, for example in siloxane polymer (PDMS) based or polyolefin (PE) based materials, the disinfectant is released through the process of polymer wearing and disinfectant diffusion. However, in the case of skin contact, the rate of PE wear is very slow and the diffusion rate slows further as the concentration of the active agent decreases. In addition, the macroscopic contamination that accumulates on the surface may totally passivate the reaction which generates the disinfection, and thus lead to unreliability, i.e. to exposure to infection.

Antimicrobial products are further described in publications EP 2 110 018, EP 0 453 112, JP H1121400, WO 2006/013374, WO 2007/0674949 and EP 0290739.

Thus, reliable destruction of pathogens in different situations, and regardless of the composition of the contamination left by a person who touches the surface, requires control of both the macroscopic and the microbiological contamination. Further examination of the situation points to a possible solution with regard to the macroscopic dirt, specifically a surface that remains clean, or a material that wears evenly. A surface structure that always remains clean and at the same time does not wear is impossible to achieve, because the composition of a macroscopic contamination varies too much. Also, a surface that wears evenly is very challenging because it may require, for example, a structure which decomposes/is dust-like, which accordingly renders impossible the realization of the required mechanical strength. Thus the solving of the problem requires exceptional resourcefulness.

It is an aim of the present invention to eliminate at least some of the problems associated with the prior art and to provide a solution for generating surfaces which remain clean, especially microbiologically clean.

The present invention is based on the idea that, in order to form a mixture, a pure polymer that is soluble in water and one or more substances that affect the pathogens are combined. In such a composition, the polymer forms a continuous phase or matrix, from which the active agent is able of being released.

The composition may be prepared for example by mixing together 10-70 parts by weight of a water-soluble polymer and 0.1-30 parts by weight of an agent that prevents the spread of pathogens, to form a mixture which is homogeneous or comprised of micro-phases, in which case a mixture is generated in which the polymer forms a continuous phase, from which the active agent is capable of being released.

The described composition can be used as an antimicrobial covering or coating, and a substrate covered with it is suitable, for example, as an object which is used by a number of people, and the surface of which the user touches with bare hands (and which, therefore, may be contaminated by microbes, in the following also "fomite"). Examples of these are a rail, hand rail, door handle or a water tap handle, furniture, electrical switch or keyboard, or a drawing tool, such as a pen, used by a number of people.

Considerable advantages are achieved with the present solution.

The human body secretes a significant amount of water, mainly in the form of sweat, all over the body surface. Of the different body parts, the hands are major water-emitting surfaces. This leads to the fact that, during hand contact, significant amounts of water are transferred to the surface that is touched. When the touched surface comprises water-soluble materials, the surface will come off through dissolution and it will be transferred to the hand or other parts of the skin that touch the surface. Because part of the material comes off the surface via a process of dissolution, the remaining material is weakened due to, for example, porosity and thus significantly more susceptible, for example, to wear. Thus, all in all, the situation is such that as the material is dissolved, it becomes thinner in a controlled way, and releases pathogen-destroying material to the spot which is touched. In addition, macroscopic contamination does not remain on the surface, and consequently, the surface remains microbiologically clean.

The structure according to the present invention is such that the disinfecting component (for example iodine) or a corresponding substance that prevents the pathogen from spreading (for example, benzalkonium chloride or soft soap or soap) is continuously released from the continuous phase formed of the polymer, i.e. from the matrix of the composition, in such a way that the surface of the object is constantly covered by the active agent, until the object is mechanically worn away.

Most suitably, the composition of the material is adjusted so that it releases a compound which reduces exposure to the infective pathogen. Reduction of the exposure may be either based on at least the partial destruction of the pathogen, or, alternatively, based on the fact that a thin layer of a surface-active agent is formed around the pathogen, which agent is most typically an amphiphilic or electrolytic material.

The solution according to our invention, and the desired application, regarding microbiological control of public premises, transport and, in particular health care facilities, provide materials that include disinfectants which have almost immediate effect, and the releasing of which is based on dissolution or softening of a water-soluble material, and thereby also on the adherence to the skin that touches the surface. Due to the adherence to the skin, the touched surface remains clean and the skin part which touches the surface is also disinfected by itself. Because disinfectant material is transferred to the person who touches it only at the point of contact, the toxicological effect can be minimized and, at the same time, the microbiological effect can be maximized.

It should also be noted that, unlike the prior art, the present material both removes the microbes and prevents the accumulation of macroscopic dirt. Therefore, the material remains inherently clean.

Preferred embodiments that illustrate the new technology are discussed below with reference to the accompanying drawings.

FIG. 1 shows a photograph which demonstrates a microbiological colony, which is achieved by using contaminated gauzes, on a growth substrate (example 1)

As described above, according to the present solution, an antimicrobial composition is generated, which comprises an active agent that reduces the spread of pathogens, in which case the active agent is mixed with a water-soluble polymer in order to form a mixture which is homogeneous or comprised of micro-phases. In a composition such as this the polymer forms a matrix that is capable of releasing the active agent when a person touches the surface comprising the composition with a bare hand or another part of the body. As described above, the moisture contained in the skin is sufficient to partially dissolve the water-soluble polymer, in which case, as a result of the dissolution, the polymer releases the active agent.

Here, "fomite" means especially an item or an object which is capable of carrying organisms which cause infections or other unwanted physiological effects, and thus of transferring them from one person to another. A fomite is typically an object which is used by a number of people, which object presents a surface that the user touches with bare hands.

Examples of water-soluble polymers are: polyvinyl pyrrolidone, polyacrylamide, water-soluble acrylates, for example water-soluble polyacrylates and methacrylates, a water-soluble cellulose derivative, cellulose derivatives, gelatin and other biologically degradable polymers, polyvinyl alcohol and their derivatives, copolymers and terpolymers and mixtures thereof. Also, block copolymers that comprise a water-soluble polymer as one block can be considered.

A preferable choice is a water-soluble polymer which can be dissolved in moisture from the skin.

More preferably, the water-soluble polymer is hygroscopic.

In practice, it is also desirable that the polymer is dissolvable also if the surface is touched with a damp item, such as a wet towel.

Because surfaces that are susceptible to infections are used especially indoors, it is preferred that the water-soluble polymer is capable of dissolving at least in skin moisture at room temperature, most suitably approximately at 10-35° C., and at a relative humidity of preferably approximately 20-80%, in particular approximately 25-75%.

Most suitably, the microbiologically protected surfaces exhibit antimicrobial activity also at higher and lower temperatures, which occur for example in washing facilities (saunas), in hot climates, and, correspondingly, in cold storage areas.

Based on the above, in the present invention, "water-soluble" means that the solubility in water of the polymer is greater than approximately 1 $g/dm^3$, in particular greater than approximately 10 $g/dm^3$, preferably at maximum approximately 1000 $g/dm^3$.

Active agents which are suitable for the composition include quaternary ammonium compounds (for example benzalkonium chloride), alcohols having a high boiling point (typically glycols), halogen-releasing compounds (chlorine, iodo, bromine; for example iodo complex of polyvinyl pyrrolidone), as well as surface-active agents which surround the pathogens when they encounter them (for example soap and surface-active agents—in general: "surfactants"). Also, derivatives and mixtures of the above are possible active agents for use in the invention.

Other active agents include acidic substances such as peracetic acid and performic acid and mixtures thereof. It is also possible to use polyacids, especially polystyrene sulphonic acid, polyacrylic acid, superacidic compounds which are based on fluoropolymers, in particular sulphonic acid derivatives of polymers which are perfluorinated with sulphonic acid groups (PVF-SA, ETFE-SA), and sulphonic acid derivatives and carboxylic acid derivatives of chlorine-containing polymers. Also, potassium peroxymonosulphate (Virkon) and chloroxylenol are possible. Mixtures of all of the above mentioned substances, possibly together with the other substances that are mentioned above, are also possible.

Either instead of the abovementioned or along with them, it is possible to use, as active agents, sulfate or sulfite compounds, the anions of which function effectively in the degradation of the polysaccharides.

As active agents, it is also possible to use polyelectrolytes in general, and polycations, due to the negative surface charge of some pathogens. Further, phenolic compounds may be used, such as amylmetacresol and thymol and polyaminopropyl biguanide.

More preferable substances are chemical disinfectants which are commonly used in hospitals and thus well-known, such as peroxide compounds, polyethylene oxide, alcohols (ethanol and its aqueous solutions), quaternary ammonium compounds (for example benzalkonium chloride), iodine, or a derivative or a mixture thereof.

A more preferable composition comprises, as the active agent, benzalkonium chloride or iodo complex of polyvinyl pyrrolidone or a mixture of these: polyvinyl pyrrolidone as a water-soluble polymer, and possibly also hydrophobic polymer.

According to another preferred embodiment, the active agent used is soap, soft soap, such as tall oil soap, or some other salt or derivative of fatty acids, or a mixture thereof.

In general, the concentration of the active agent is less than approximately half of the total weight of the composition, its concentration is for example approximately 0.01-30%.

More preferably, the concentration of the active agent is chosen according to its LD50 value. In general, the concentration of the active agent must be below the toxic range but still within a range that is effective against the pathogens. Therefore, a necessary and safe concentration is chosen on the basis of the rate of wearing and the antipathogenic effect (toxicity) of the active agent.

Preferably, the concentration of the active agent is chosen in order that the person who touches the object that has the composition on its surface is exposed to an amount of material which is released through the wearing of the composition, which amount is at maximum $1/1000$, especially at maximum $1/5000$, most suitably at maximum $1/10000$, of the LD50 value determined for the substance.

Thus, for example for benzalkonium chloride approximately 1-10% by weight is a suitable range, for the composition of an iodo complex of polyvinyl pyrrolidone 0.1-2.5% by weight is a suitable range, and for tall oil soap, a suitable range is typically 10-25% by weight.

In a more preferred embodiment, the composition comprises
  10-70 parts by weight of a water-soluble polymer, and
  0.1-30 parts by weight of a component (one substance or a mixture of two or more substances) preventing the spread of pathogens.

According to another preferred embodiment, the composition further comprises a hydrophobic polymer such as a thermoplastic. Thermoplastics include polyolefins, polystyrene, polyesters, polyamides, polynitriles, polyvinyl chloride, copolymers such as ABS, and other materials that possess good mechanical properties.

Most suitably, the composition comprises 5-80 parts by weight of a hydrophobic polymer. More preferably, the percentage of the hydrophobic component is less than 75% by weight, in particular its percentage is at maximum 70% by weight, most suitably 65% by weight, preferably 60% by weight or less, for example at maximum 50% by weight.

The compositions comprise for example approximately 0-65 parts per weight, particularly 5-50 parts by weight of a hydrophobic polymer, approximately 20-50 parts by weight of a water-soluble polymer, and 1-30 parts by weight of a component that prevents the spread of the pathogens. Preferably, based on the weight, the composition comprises more water-soluble polymer than component that prevents the spread of the pathogens.

Particular examples that may be mentioned are compositions which comprise 20-60 parts by weight of a hydrophobic polymer, 20-50 parts by weight of a water-soluble polymer and 1-20 parts by weight of a component that prevents the spread of the pathogens. In addition, to the hydrophobic polymer being a thermoplastic, particularly a thermoplastic which is mixed with a water-soluble polymer, it is also possible to introduce a hydrophobic polymer or polymer share to form a part of the water-soluble polymer. Thus, in one embodiment, the hydrophobic polymer is in the form of a copolymer which comprises hydrophobic monomers. In another embodiment, the hydrophobic polymer or polymer share is in the form of a block copolymer, which comprises hydrophobic polymer blocks. Most suitably, the remainder of the copolymer or block copolymer is comprised either partly or totally of water-soluble components (monomers or polymer blocks).

Most suitably, the polymer components of the composition are chosen in order to furnish the composition with self-supporting properties. "Self-supporting" means that a composition that is processed to form a strip or a sheet, which is at least 1 mm thick and at least 30 mm long, does not bend when horizontal and supported at one end.

In one embodiment, the quantity of the hydrophobic polymer is, measured in parts per volume, at least as great as the percentage of the water-soluble polymer.

As an example of an interesting solution, which is suitable, for example, for manufacturing medical instruments, a composition can be mentioned which comprises 50-75 parts by weight of polystyrene, 20-35 parts by weight of polyvinyl pyrrolidone and 1-10 parts by weight of benzalkonium chloride.

More preferably, the polymer components of the composition are chosen so that they are melt-processible, for example by die-casting, in which case the polymer composition can be shaped into the form of a utility item, such as furniture, an electrical switch or a keyboard, or part of that item. It is also possible to prepare the composition to be a processed product, for example, an elongated extrudate or an otherwise processed object, which has the shape of a tube, strip, sheet or film. More preferably, the prepared product is self-supporting.

The above-described polymer product can be used to cover and coat different objects, or in general as part of them (as the surface layer).

In addition to the above-mentioned components, in one embodiment the composition comprises an additive which enhances the effect of the active agent in reducing the spread of the pathogen, for example, a polycation or its derivative comprising counterions, or a metal or metal ion. Examples of metals are transition element metals and precious metals, and salts and mixtures thereof.

Generally, the amount of additives is approximately 0.01-5% of the total weight of the composition.

The composition can be prepared by mixing the components of the composition. It is possible to add all at once, or two or more components. In one embodiment, the water-soluble polymer and the active agent are first mixed with each other. In another embodiment, the active agent and the hydrophobic polymer are mixed with each other. Generally, 10-70 parts by weight of a water-soluble polymer, 0.1-30 parts by weight of a component which prevents the spread of pathogens, and 5-80 parts by weight of a hydrophobic polymer are mixed.

In one embodiment, the components are mixed together at an elevated temperature, which is higher than the melting temperature of the water-soluble polymer.

The present method may be implemented, for example, by melt mixing, preferably in a melt processing apparatus, such as an extruder.

The most important properties of the macroscopic composition of the material that prevents infection by the pathogens are the following: the material should become thinner at an appropriate rate, in order to avoid the accumulation of contamination on the surface of the object, and the antidote which acts regarding the released pathogens should be such that its possible reaction with other raw materials does not adversely affect its performance.

In one application, the composition of the material is adjusted by means of both the overall composition and the melt-processing conditions so that, in use, wear of the material essentially demands dissolution of the water-soluble components. If the composition comprises hydrophobic material, the surface of the material becomes slightly porous as the material dissolves. The degree of porosity and the mechanical properties of the porous phase, however, can be adjusted so that the porous phase wears mechanically at the same rate as the actual dissolution takes place and, consequently, the agent which affects the pathogens is released at a constant rate until the object is worn away.

Preferably, a pure, hydrophilic polymer and one or more of the agents that affect the pathogens, are combined, in order to form a mixture which is a homogeneous mixture, or one which has a structure that is composed of microphases. In such a composition, the polymer forms a matrix, from which the active agent is able to release itself. This alternative requires the main component to possess a suitable hydrophilicity so that the material dissolves without excessive swelling and water absorption from the surrounding air or in connection with a possible cleaning. Preferably, the dissolution takes place at a suitable rate.

It is well known that mechanical cleaning by means of a damp cloth or the like is currently used as a basic method in hospitals; however, as such, it does not prevent pathogens from being transferred, because the cleaning is carried out, for example, once a day.

The following examples illustrate the use of the present composition as an antimicrobial covering or coating or as a part of the surface. The surface or substrate to be treated is typically an object that is exposed to infection by pathogens, i.e. a fomite. These are objects which are used by a number of people, which object presents a surface which the user touches with bare hands, such as a rail, door handle or tap handle, furniture, electrical equipment switch or a keyboard.

More preferably, the present product forms the surface of a fomite, either partially or preferably completely.

EXAMPLE 1

Compositions

The following compositions are prepared by mixing the components with each other in an extruder:

1) 54% by mass of Septon 2063, 40% polyvinyl pyrrolidone, 6% benzalkonium chloride
2) 74% by mass of Septon 2063, 20% polyvinyl pyrrolidone, 6 PVP iodo
3) 70% by mass of polystyrene, 25% polyvinyl pyrrolidone, 5% benzalkonium chloride
4) 50% by mass of Septon 2063, 37% PVP, 8% tall oil soap, 5% benzalkonium chloride
5) 48% by mass of Septon 2063, 40% PVP, 12% tall oil soap
[Septon 2063—Styrene Ethylene Propylene Styrene Block Copolymer (SEPS)]

EXAMPLE 2

Solution Functionality

Tubular objects, which are prepared by extruding (temperature approximately 95-110 degrees) from raw materials according to composition example 1 (i.e. the composition 1 of example 1), were examined for microbiological purity as follows. Both benzalkonium chloride-bearing and benzalkonium chloride free objects were touched with unwashed hands, and after that, sterile pieces of gauze were placed onto the surfaces of the objects, in order to transfer surface contaminations. Finally, the pieces of gauze in question were moved to microbiological cultivation substrates.

After incubation (33° C., 24 h), the microbiological purities of the microbiological cultivation substrates were examined visually. FIG. 1 is an example of the result of the test on the substrates after the incubation, and during this test the contaminated gauzes were tested without them being purified microbiologically.

Microbiological tests which are described above were carried out for a period of approximately 40 days using the same tubular test objects, during which time approximately 30 samples were taken from each test object. Some of the samples were taken immediately, and some after different periods of time (15-45 min) following the contamination, in order to determine the disinfection rate. Tables 2 and 3 show a summary of the results of the tests.

TABLE 1

Microbiological purity without contamination of the gauze used for contamination transfer

| Date | Test result |
| --- | --- |
| 24 May 2013 | 0 |
| 4 Jun. 2013 | 1 |
| 6 Jun. 2013 | 0 |
| 13 Jun. 2013 | 0 |
| 19 Jun. 2013 | 0 |
| 28 Jun. 2013 | 1 |
| 4 Jul. 2013 | 1 |

Test result 0 indicates a microbiologically pure sample, and 1 indicates microbiological growth, i.e. contamination.

Samples were taken from the objects approximately 30 minutes following contamination, which gave the microbiologically passivating agent time to impact on the contamination for the same duration of time.

The results are shown in Table 2. Test result 0 indicates a microbiologically pure sample, and 1 indicates microbiological growth, i.e. contamination.

TABLE 2

Results of the microbiological tests performed on the example composition 1 and its reference sample (object not comprising benzalkonium chloride) (determined 30 minutes after contamination)

| Date | Reference object | Composition 1 |
| --- | --- | --- |
| 24 May 2013 | 1 | 0 |
| 4 Jun. 2013 | 1 | 0 |
| 6 Jun. 2013 | 0 | 0 |
| 13 Jun. 2013 | 1 | 0 |
| 19 Jun. 2013 | 0 | 0 |
| 28 Jun. 2013 | 1 | 0 |
| 4 Jul. 2013 | 1 | 0 |

Microbiological samples were taken from the objects immediately after contamination. The results are shown in Table 3. Test result 0 is a microbiologically pure sample, and 1 indicates microbiological growth, i.e. contamination.

TABLE 3

Results of the microbiological tests performed on the example composition 1 and its reference sample (object not comprising benzalkonium chloride) (determined 30 minutes after contamination)

| Date | Reference object | Composition 1 |
| --- | --- | --- |
| 24 May 2013 | 1 | 0 |
| 4 Jun. 2013 | 1 | 0 |
| 6 Jun. 2013 | 1 | 0 |
| 13 Jun. 2013 | 1 | 0 |
| 19 Jun. 2013 | 1 | 0 |
| 28 Jun. 2013 | 1 | 0 |
| 4 Jul. 2013 | 1 | 0 |

According to the results shown in Table 2 and 3, the benzalkonium chloride comprised in composition 1 generated a microbiological disinfection, both immediately and during a period of approximately 30 min. Thus, the test results indicate that the disinfectant effect of the benzalkonium chloride is immediate and that it is released at a sufficiently high rate, during a period of at least approximately one and a half months, despite the fact that the test object was touched with a normal grip of the hand more than a hundred times.

EXAMPLE 3

Field Test Performed on Plastic Surfaces which Contain Benzalkonium Chloride

Field testing of plastic surfaces which contain benzalkonium chloride were carried out in a hospital. The total number of samples was 54 objects in these microbiological tests, with both active (S) and reference samples (C), i.e. a total of 108 samples. After incubation, the total number of microbial colonies (CFU) of each sample was examined.

TABLE 4

Summary of the total microbe test results of the tested reference samples (C1-6) and the antimicrobial test samples (S1-6). The results include both the average value and the standard deviation.

| | Sample | | | | | |
| --- | --- | --- | --- | --- | --- | --- |
| | C1 | C2 | C3 | C4 | C5 | C6 |
| Department | Thoracic | Thoracic | Thoracic | Surgical emergency | Surgical emergency | Surgical emergency |
| Average val. | 56.5 | 46.2 | 69.2 | 53.8 | 46.5 | 64.4 |
| Standard dev. | 33.0 | 49.9 | 36.6 | 30.7 | 24.5 | 27.5 |
| Näyte | S1 | S2 | S3 | S4 | S5 | S6 |
| Osasto | Neurology | Neurology | Neurology | Heart surg. | Heart surg. | Heart surg. |
| Keskiarvo | 6.3 | 17.1 | 1.7 | 2.4 | 1.1 | 0.1 |
| Keskipoikk. | 11.2 | 28.3 | 1.8 | 4.0 | 2.2 | 0.3 |

As the above results show, the active samples (S1-6) did not indicate any significant change in functionality (activation or passivation). In fact, the active samples S1-6 were exceptionally clean throughout the test period.

Of the active samples S1 and S2, one showed 3 pure samples (up to 1 CFU) and the other 4 pure samples. The reference samples showed a significant amount of CFU.

TABLE 5

Microbiological purity of the active samples S1-6 (54 test results)

| CFU reading | Number of tests | % share of total number of tests | Cumulative % share |
|---|---|---|---|
| 0 | 23 | 43 | 43 |
| 1 | 11 | 20 | 63 |
| 2 | 4 | 7 | 70 |
| 3 | 4 | 7 | 78 |

Based on the results, it can be seen that if the infection risk limit is less than 1 CFU, then, according to the present technology, the risk of infection can be reduced by almost half, and if the CFU limit is a maximum of 3, the risk of infection is reduced by approximately 80%.

The invention claimed is:

1. An object comprising an antimicrobial surface, wherein the antimicrobial surface comprises an antimicrobial composition, the antimicrobial composition comprising:
   1-30 parts by weight an active agent that reduces a spread of pathogens, wherein the active agent is mixed with 20-50 parts by weight of a water-soluble polymer and 5-50 parts by weight of a hydrophobic polymer, in order to produce a mixture in which the polymer forms a continuous phase, from which the active agent is released,
   wherein, upon repeated contact with a second object comprising an amount of moisture, the antimicrobial surface both wears mechanically and dissolves to release the active agent as the antimicrobial surface becomes thinner, and
   wherein the object comprises a fomite capable of contact with human skin.

2. The object according to claim 1, wherein the object comprises a fomite capable of repeated touch with bare hands of a user.

3. The object according to claim 1, wherein the hydrophobic polymer comprises a member from the group consisting of a thermoplastic which forms a mixture with the water-soluble polymer, a copolymer comprised of hydrophobic monomers, or a block copolymer comprised of hydrophobic polymer blocks.

4. The object according to claim 3, wherein the amount of the hydrophobic polymer present is effective to furnish the composition with self-supporting properties.

5. The object according to claim 1, wherein the active agent is selected from group consisting of quaternary ammonium compounds, glycols, halogen-releasing compounds, soap and surface-active agents, peroxide compounds, peracetic acid, performic acid, polyacids, sulphonic acid derivatives, and carboxylic acid derivatives of polymers that comprise chlorine, potassium peroxymonosulphate, chloroxylenol, sulphate or sulphite compounds, polyelectrolytes, polycations, phenolic compounds, polyaminopropyl biguanide, soft soap, tall oil soap, salts or derivatives of fatty acids or resin acids, and combinations of the above.

6. The object according to claim 1, wherein the active agent is selected from the group consisting of benzalkonium chloride, an iodo complex of polyvinyl pyrrolidone, and a mixture thereof.

7. The object according to claim 1, wherein the active agent is selected from the group consisting of soap, tall oil soap, a salt or derivative of a fatty acid, and combinations thereof.

8. The object according to claim 1, wherein the antimicrobial surface is in the form of an elongated extrudate.

9. The object according to claim 1, wherein the hydrophobic polymer comprises a thermoplastic polymer.

10. The object according to claim 1, wherein the second object comprises a human hand.

* * * * *